US010307644B2

(12) United States Patent
Jones et al.

(10) Patent No.: US 10,307,644 B2
(45) Date of Patent: Jun. 4, 2019

(54) VIRTUAL COMPETITION ENVIRONMENT

(71) Applicant: Halcyonic, LLC, Akron, OH (US)

(72) Inventors: Simeon Jarrod Jones, Akron, OH (US); Elias Micah Jones, Cypress, TX (US)

(73) Assignee: Halcyonic, LLC, Akron, OH (US)

( * ) Notice: Subject to any disclaimer, the term of this patent is extended or adjusted under 35 U.S.C. 154(b) by 338 days.

(21) Appl. No.: 15/284,882

(22) Filed: Oct. 4, 2016

(65) Prior Publication Data

US 2017/0050081 A1 Feb. 23, 2017

Related U.S. Application Data

(63) Continuation-in-part of application No. 14/072,516, filed on Nov. 5, 2013, now abandoned.

(51) Int. Cl.
*A63F 9/00* (2006.01)
*A63B 24/00* (2006.01)
*G07F 17/32* (2006.01)
*A63F 13/795* (2014.01)
*G16H 20/30* (2018.01)

(52) U.S. Cl.
CPC ...... *A63B 24/0084* (2013.01); *A63B 24/0062* (2013.01); *A63B 24/0075* (2013.01); *A63F 13/795* (2014.09); *G07F 17/3225* (2013.01); *G07F 17/3244* (2013.01); *G07F 17/3295* (2013.01); *G16H 20/30* (2018.01); *A63B 2024/0065* (2013.01); *A63B 2220/83* (2013.01)

(58) Field of Classification Search
None
See application file for complete search history.

(56) References Cited

U.S. PATENT DOCUMENTS

| 6,824,462 B2 | 11/2004 | Lydon et al. |
| 8,663,017 B1 * | 3/2014 | Smyth ............... G06Q 99/00 463/40 |
| 9,707,474 B1 * | 7/2017 | Cardinale ............ A63F 13/213 |
| 10,065,074 B1 * | 9/2018 | Hoang ............... A63B 24/0003 |

(Continued)

OTHER PUBLICATIONS

International Search report and Written opinion cited in PCT/US2014/063070 dated Jan. 29, 2015, 8 pages.

*Primary Examiner* — Seng Heng Lim
(74) *Attorney, Agent, or Firm* — Cooper Legal Group, LLC

(57) ABSTRACT

One or more techniques and/or systems are provided for facilitating a virtual competition environment. One or more users may register for access to the virtual competition environment in order to compete in various types of activities, such as workout activities, dance activities, real-world activities, and/or virtual activities. A user may be provided with activity assignments, user created activities, and/or challenge activities between groups of users through the virtual competition environment (e.g., the virtual competition environment may be accessible through a website, a mobile app, etc.). The user may upload activity results for activity assignments, which may be evaluated and/or ranked against how other users performed such activity assignments. The user may register as a judge in order to evaluate and/or rank activity results (e.g., evaluate videos of users performing an activity). Users and/or judges may be rewarded for participating in activities and/or judging activities.

20 Claims, 14 Drawing Sheets

(56) References Cited

U.S. PATENT DOCUMENTS

| | | |
|---|---|---|
| 2002/0115488 A1 | 8/2002 | Berry et al. |
| 2003/0027639 A1 | 2/2003 | Peterson et al. |
| 2007/0191101 A1 | 8/2007 | Coliz et al. |
| 2009/0118100 A1* | 5/2009 | Oliver ................ A63B 24/0062 482/8 |
| 2009/0318267 A1* | 12/2009 | Park ........................ A61H 3/00 482/8 |
| 2010/0004055 A1 | 1/2010 | Gormley et al. |
| 2010/0279827 A1 | 11/2010 | Farnsworth et al. |
| 2011/0207581 A1* | 8/2011 | Flaction .................. A61B 5/22 482/8 |
| 2012/0183940 A1* | 7/2012 | Aragones ............ G06F 19/3481 434/247 |
| 2012/0185484 A1 | 7/2012 | Jones et al. |
| 2012/0277891 A1* | 11/2012 | Aragones ............ G06F 19/3481 700/91 |
| 2013/0143669 A1 | 6/2013 | Muller |
| 2013/0203480 A1 | 8/2013 | DeYoung |
| 2013/0338802 A1* | 12/2013 | Winsper .............. G06F 19/3481 700/92 |
| 2014/0074265 A1* | 3/2014 | Arginsky ........... A63B 71/0622 700/91 |
| 2015/0057128 A1* | 2/2015 | Ishii .................... A63B 24/0087 482/8 |
| 2015/0127127 A1* | 5/2015 | Carpenter .......... G06Q 30/0631 700/92 |
| 2016/0023043 A1* | 1/2016 | Grundy .............. A63B 24/0062 482/8 |
| 2017/0038771 A1* | 2/2017 | Green .................. G05D 1/0016 |
| 2017/0173391 A1* | 6/2017 | Wiebe .................. A61B 5/0022 |
| 2017/0274249 A1* | 9/2017 | Moebius .......... A63B 21/00845 |
| 2017/0368413 A1* | 12/2017 | Shavit ................ A63B 24/0075 |

* cited by examiner

VIRTUAL COMPETITION ENVIRONMENT

RELATED APPLICATION

This application claims priority to and is a continuation-in-part of U.S. application Ser. No. 14/072,516, filed on Nov. 5, 2013, entitled "VIRTUAL COMPETITION ENVIRONMENT", which is incorporated herein.

BACKGROUND

Many users engage in various types of competitions, such as road races, dance competitions, weight lifting competitions, workout competitions crafting competitions (e.g., building a sculpture, building a toothpick bridge, etc.), skateboarding competitions, fashion competitions, videogame competitions, and/or a wide variety of other activities with which users may compete. In an example, a fantasy football league may allow users to create fantasy football teams that may be tracked through an online interface and/or a pen and paper methodology. Such users may pay fees in order to participate in the fantasy football league, and the winner may be awarded a payout from such fees.

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

Among other things, one or more systems and/or techniques for facilitating a virtual competition environment are provided. In an example, the virtual competition environment may be accessible from various devices of users (e.g., an app deployed on a mobile device; a website accessible through a personal computer; a cloud service accessible to sports watches, GPS devices, tablet devices, videogame consoles, and/or other electronic devices; etc.). Users may register with the virtual competition environment in order to compete in various activities and/or judge activity results of users. The virtual competition environment may group users into skill groups based upon various information (e.g., historical activity result data; user supplied information such as age, weight, etc.; social network information about the user; an output wattage derived from a power output calculation regarding physical capabilities of a user; etc.). In this way, users may compete against similarly skilled users when performing an activity assignment. Groups of users may compete against one other when performing activities, such as members of a first gym competing against members of a second gym. In an example, a user may create a user created activity that may be performed by other users. In an example, a user may register as a judge in order to judge activity results of users (e.g., the judge may review a video of a user performing pushups in order to determine whether the user performed the pushups correctly). Users may be rewarded/compensated based upon how users rank against other users that competed in an activity assignment (e.g., a top 3 users may be awarded credits to pay for future activity assignments, monetary compensation, and/or charity donations), and judges may be rewarded/compensated for judging activity results. The virtual competition environment may comprise a social network and/or may be socially integrated into other social networks (e.g., a user may share activity results; challenge other users; send messages to users; etc.)

In an example, a first user may register for access to the virtual competition environment (e.g., the first user may register a mobile device, such as a smart phone, tablet device, camera, sports watch, a videogame console, etc.). The first user may be provided with a first activity assignment. For example, the first user may be grouped into an intermediate skill group for workout activities based upon various information about the first user (e.g., a power output metric derived from various measurements of the first user, such as a shoulder width, an arm length, a height, workout results such as pull-ups, thrusters, etc.; historical activity results and rankings for the user; etc.). The first activity assignment may be tailored for the intermediate skill group, and thus may be provided to the first user and/or other users within the first skill group. A first activity result may be received from the first user for the first activity assignment (e.g., a number of sit-ups, a time to complete the sit-ups, a video of the user performing the sit-ups, identifying information for the first user, and/or other information regarding a sit-up activity assignment). The first activity result may be evaluated to assign a first activity rank for the first user with regard to the first activity assignment. In an example, the first activity result, such as the video, may be provided to a judge that may evaluate the first activity result. In another example, the number of sit-ups and the time to complete the sit-ups may be evaluated against activity results of other users (e.g., within the intermediate skill group). In this way, the first activity rank may be assigned to the first user for the first activity assignment. If the first activity rank is above a reward threshold, then a reward (e.g., credits to purchase activity assignments; money; a charity donation; etc.) may be provided to the first user. The first user may view the first activity rank, the first activity result, and/or other historical activity data for the user and/or other users, such as through a social network for the virtual competition environment.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
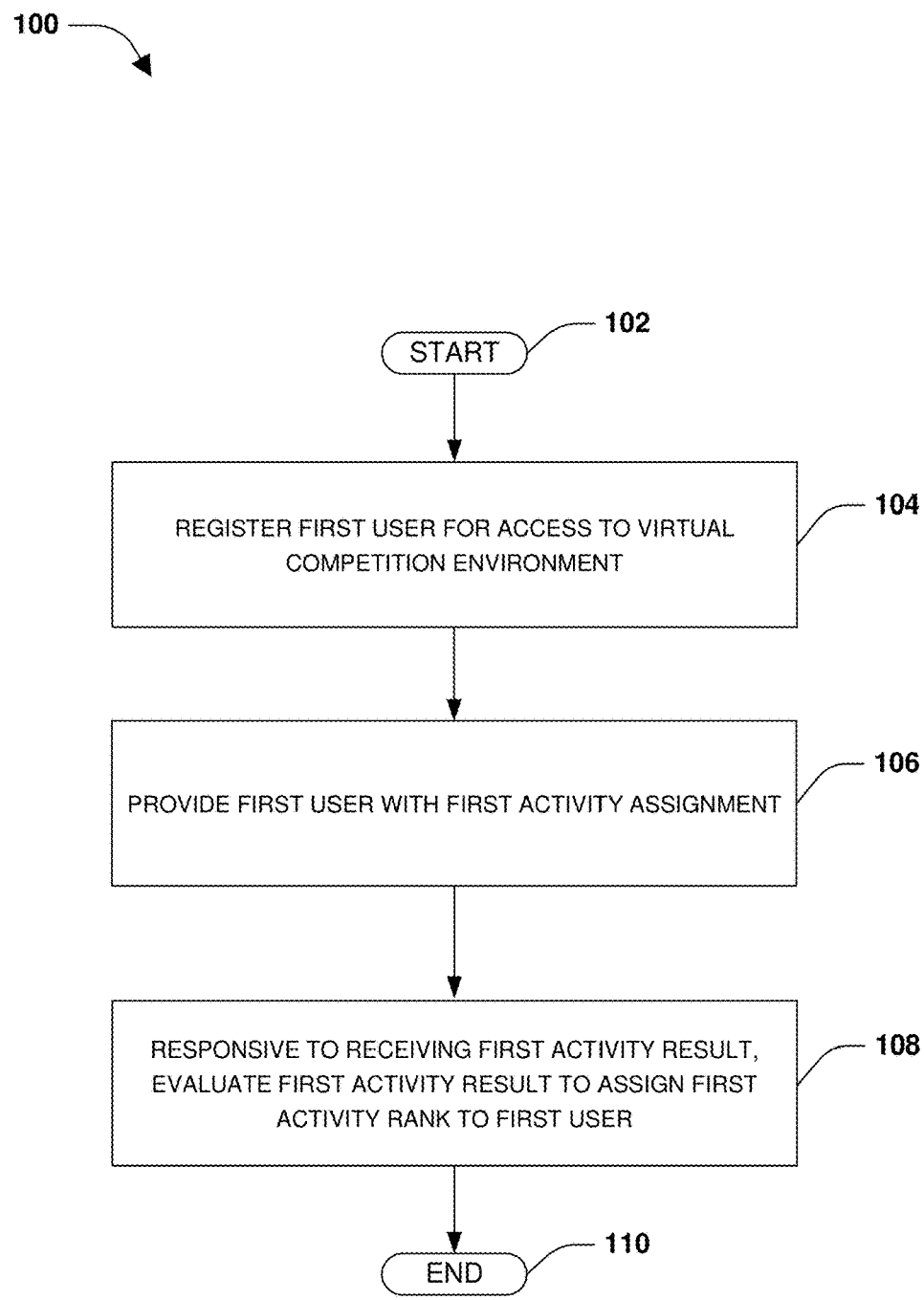
FIG. 1 is a flow diagram illustrating an exemplary method of facilitating a virtual competition environment.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

An embodiment of facilitating a virtual competition environment is illustrated by an exemplary method 100 of FIG. 1. At 102, the method starts. A virtual competition environment may provide an environment or interface through which users may register to perform activities (e.g., compete with other users or themselves), such as workout activities (e.g., a weightlifting competition, a running competition, an exercise competition, etc.), dance activities (e.g., a dance studio competition, a singing competition, etc.), school project activities (e.g., a science fair project), videogame activities (e.g., achieving a particular score, completing an objective within a certain time, locating an item, defeating a boss, etc.), crafting activates (e.g., creating a sculpture), cooking assignments (e.g., decorating a cake), item construction activities (e.g., building a catapult), real world activities (e.g., performing a work-related activity for payment, such as creating and mailing fliers), virtual world activities (e.g., performing internet related activities, such as advertising activities, reviewing products, testing software, creating or reviewing an app for an app store, etc.), and/or a wide variety of other activities that may be monitored and/or tracked through the virtual competition environment. The virtual competition environment may be hosted such that users may register with and/or access the virtual competition environment from various devices (e.g., the virtual competition environment may be accessible from an application, a mobile app, a website, a web service, a cloud service, a sports watch, an automobile device, etc.).

At 104, a first user may be registered for access to the virtual competition environment. In an example, the first user may be assigned (e.g., and/or later reassigned) to a first skill group based upon a user profile (e.g., the user may specify an ability to perform an activity; the user may specify physical attributes of the user, which may be used to determine an output wattage for the first user; social network information may be extracted; historical activity results data as to how the user performed activities may be evaluated; and/or a wide variety of other identifying information for the user). One or more other users may be assigned to the first skill group, such as an expert skill group, such that users within the first skill group may be provided with activity assignments that may be tailored to abilities of such users. Users may be ranked against other users within the first skill group based upon how the users perform activity assignments.

At 106, the first user may be provided with a first activity assignment. In an example, the first activity assignment may be provided to the first user for free. In another example, the first activity assignment may be purchased by the first user in exchange for credits and/or monetary payment (e.g., a credit purchasing interface may be provided to the first user, such that the first user may purchase credits used for participating in activity assignments). In another example, the first activity assignment is provided to the one or more users assigned to the first skill group. In another example, the first activity assignment may be assigned to a threshold number of users within the first skill group, and when the threshold is met, the first activity assignment may be "closed" and a new iteration of the first activity assignment may be generated to create a new first activity assignment. The new first activity assignment may be provided to users within the first skill group until the threshold is met. In this way, one or more iterations of the first activity assignment may be provided to users so that users within an iteration may be ranked against one another and/or ranked across iterations.

At 108, a first activity result for the first activity assignment may be received from the first user. In an example, the first user may submit textual information describing performance of the first activity assignment (e.g., a number of repetitions and/or a time to perform a workout activity). In another example, the first user may submit an image (e.g., a series of time stamped photos illustrating various stages of creating a cake). In another example, if the first user has a participant rank above a threshold (e.g., the first activity result for the first activity assignment may be above a threshold such as a top 15% of users; historical activity results for the first user may indicate that the first user has a historical participant rank above the threshold; etc.), the first user may be requested to submit a video of the first user performing the first activity assignment. It may be appreciated that a wide variety of information may be received as the first activity result (e.g., GPS information, a video clip from playing a videogame, temporal information, an audio recording, etc.).

The first activity result may be evaluated to assign a first activity rank for the first user with regard to the first activity assignment. In an example, a completion time and/or a number of repetitions/sets for a workout activity may be compared with activity results of other users (e.g., compared against a set of activity results received from one or more users within the first skill group, such as users within the same iteration of the first activity assignment that was provided to the first user), such that the first user may be ranked against the other users. In an example, the first activity result may be provided to a judge registered with the virtual competition environment (e.g., a certified workout user, a certified builder, a certified chef, a professor, a person having a relatively extensive knowledge basis with regard to an activity, etc.). For example, a video of the first activity result may be provided to the judge for evaluation of the video. In an example, an evaluation time limit may be provided to the judge. The evaluation time limit may specify a time by which the judge is to accept, reject, and/or assign an activity rank for the video. The judge may be instructed to verify that the first user utilized a valid video for the first activity assignment (e.g., verification of a clock within the video; verification of a user id spoken by the first user; verification of a technique used to perform the activity; etc.). In this way, the judge may evaluate the first activity result (e.g., through a judge review interface provided to the judge), which may be used to assign the first activity rank to the first user. If the judge rejects the video, then an appeal process may be facilitated for the first user (e.g., resubmission of the video to a new judge; additional verification for the video; etc.). The judge may be compensated for judging the video, such as with a credit used to participate in activities, a monetary reward, and/or a donation to a charity selected by the judge.

In an example, a reward may be provided to the first user based upon the first activity rank. For example, the reward may comprise a credit used to participate in other activities, a monetary reward, and/or a donation to a charity selected by the first user. An amount/value of the reward may be proportional to the first activity rank (e.g., a larger reward may be provided for relatively higher activity ranks). In an example, a first user profile for the first user may be generated (e.g., and/or updated where the first user profile already exists) based upon activity results and/or activity ranks associated with the first user, such as the first activity rank for the first activity result. The user may access the first user profile, historical activity results, and/or historical activity ranks through a performance interface. In this way, the first user may track how the first user performed various activities, compare how the first user ranks against other users (e.g., users within an iteration of an activity assignment; users within the first skill group; any registered user; etc.), and/or track statistical data derived from historical activity results of the user (e.g., calories burned for a type of activity or a time period; increase/decrease in strength; accuracy of cake decorating; etc.).

In an example, the first activity result and/or the first activity rank may be shared (e.g., internally through the virtual competition environment and/or externally through another source) through a social network, a website, a leader board, an instance of the virtual competition environment on a device of a second user (e.g., as a push notification to other users registered with the virtual competition environment), etc. For example, a social network interface may be provided to users of the virtual competition environment. The social network interface may provide friends list functionality, messaging functionality, rank comparison functionality, activity information, activity results information, activity sharing functionality (e.g., share or suggest an activity assignment with a second user), challenge invitation functionality (e.g., a group of users may challenge another group of users in an activity assignment), and/or social profile functionality.

In an example, user activity creation functionality may be provided to users of the virtual competition environment. For example, a first user created activity may be received from the first user (e.g., the first user may specify various parameters for a workout challenge, such as repetitions, weight values, time constraints, etc.). In an example, the first user may specify whether rewards from participating in the user created activity are to be donated to charity, paid out to users above a threshold rank, etc. The user created activity may be provided to one or more users registered with the virtual competition environment (e.g., the workout challenge may be provided to a first gym and a second gym in order to facilitate a competition between the first gym and the second gym; the workout challenge may be provided to users within the first skill group; etc.).

In an example, activities may be facilitated between groups of users (e.g., a competition between gyms, bakeries, dance studios, schools, art studios, etc.). For example, a first user may be assigned to a first user group based upon the first user having membership to the first user group (e.g., the first user may belong to a first gym). A challenge activity may be generated between the first user group and a second user group (e.g., one or more registered users of a second gym). Activity results from the first user group may be ranked with activity results from the second user group to assign rankings to the first user group, the second user group, one or more users that are members with the first user group, and/or one or more users that are members with the second user group. In this way, users and/or groups of users may compete and/or be ranked against one another through the virtual competition environment. At 110, the method ends.

Figure 2:
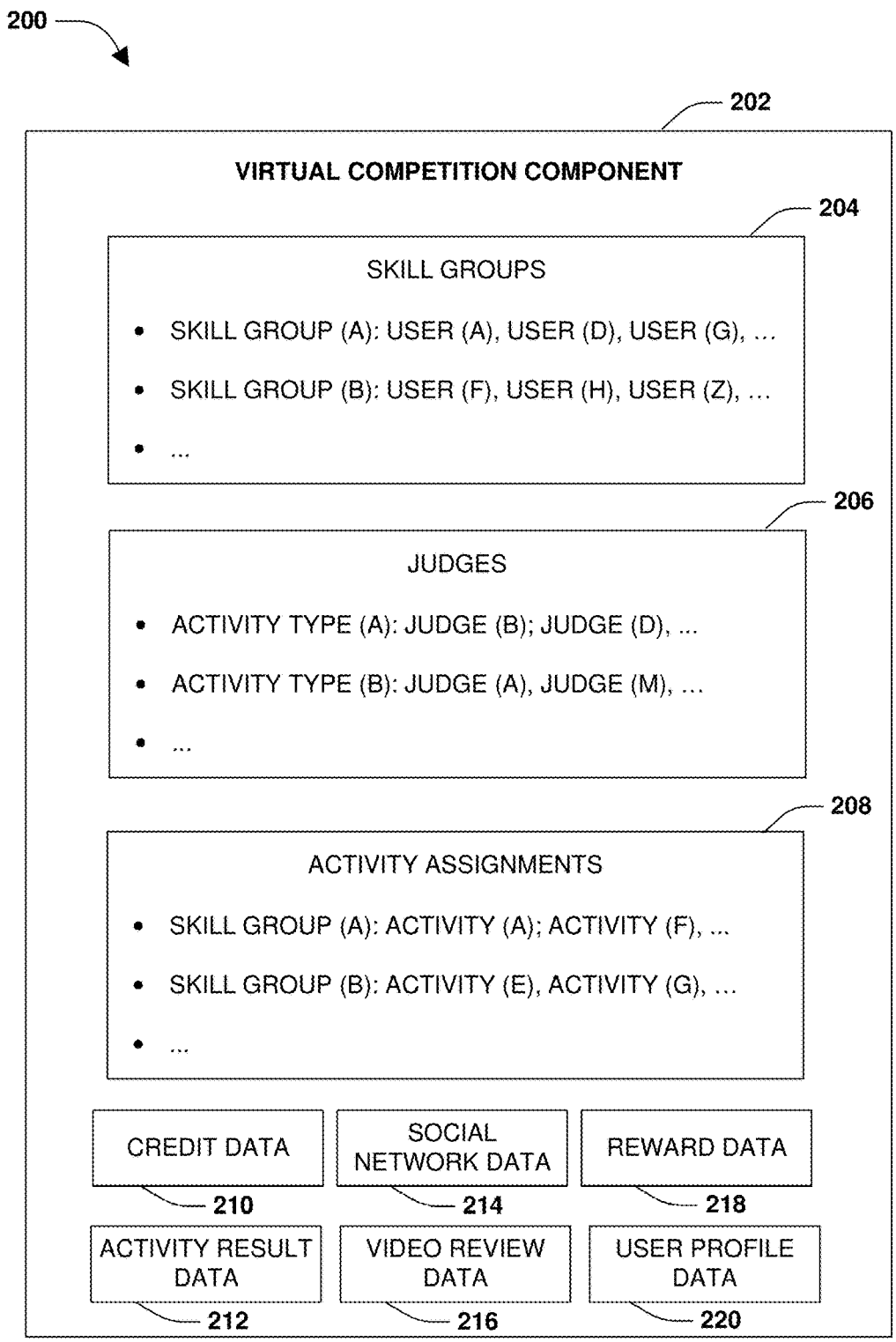
FIG. 2 is a component block diagram illustrating an exemplary system for facilitating a virtual competition environment.

FIG. 2 illustrates an example of a system 200 for facilitating a virtual competition environment. The system 200 may comprise a virtual competition component 202. The virtual competition component 202 may be configured to register users for access to the virtual competition environment. The virtual competition component 202 may be configured to group users into skill groups 204 based upon various information associated with such users (e.g., user (A), user (D), use (G), and/or other users may be grouped into skill group (A) because such users have relatively similar workout abilities). The virtual competition component 202 may be configured to provide activity assignments 208 to users (e.g., a user may purchase activity credits, tracked within credit data 210, which may be used to participate in and/or create activity assignments). For example, an activity assignment (A), an activity assignment (F), and/or other activity assignments may be assigned to users within skill group (A). Activity result data 212 may be collected from users that participate in activity assignments 208. The virtual competition component 202 may utilize judges 206 to evaluate and/or rank users that submit activity results for activity assignments (e.g., a judge (B) and a judge (D) may be available to evaluate activity results for an activity type (A) such as swimming activities; judge (A) and judge (M) may be available to evaluating activity results for an activity type (B) such as running activities; etc.). For example, video review data 216, such as user submitted videos of activity results, may be provided to judges for evaluation of activity results. The virtual competition component 202 may be configured to maintain reward data 218 corresponding to rewards (e.g., credits, charity donations, money) provided to users for participating in activities and/or to judges 206 for evaluating activity results. User profile data 220 may be maintain for users based upon performance of activity assignments (e.g., activity ranking information, activity results, etc.). The virtual competition component 202 may maintain social network data 214 through which users of the virtual competition environment may interact and/or share information.

Figure 3:
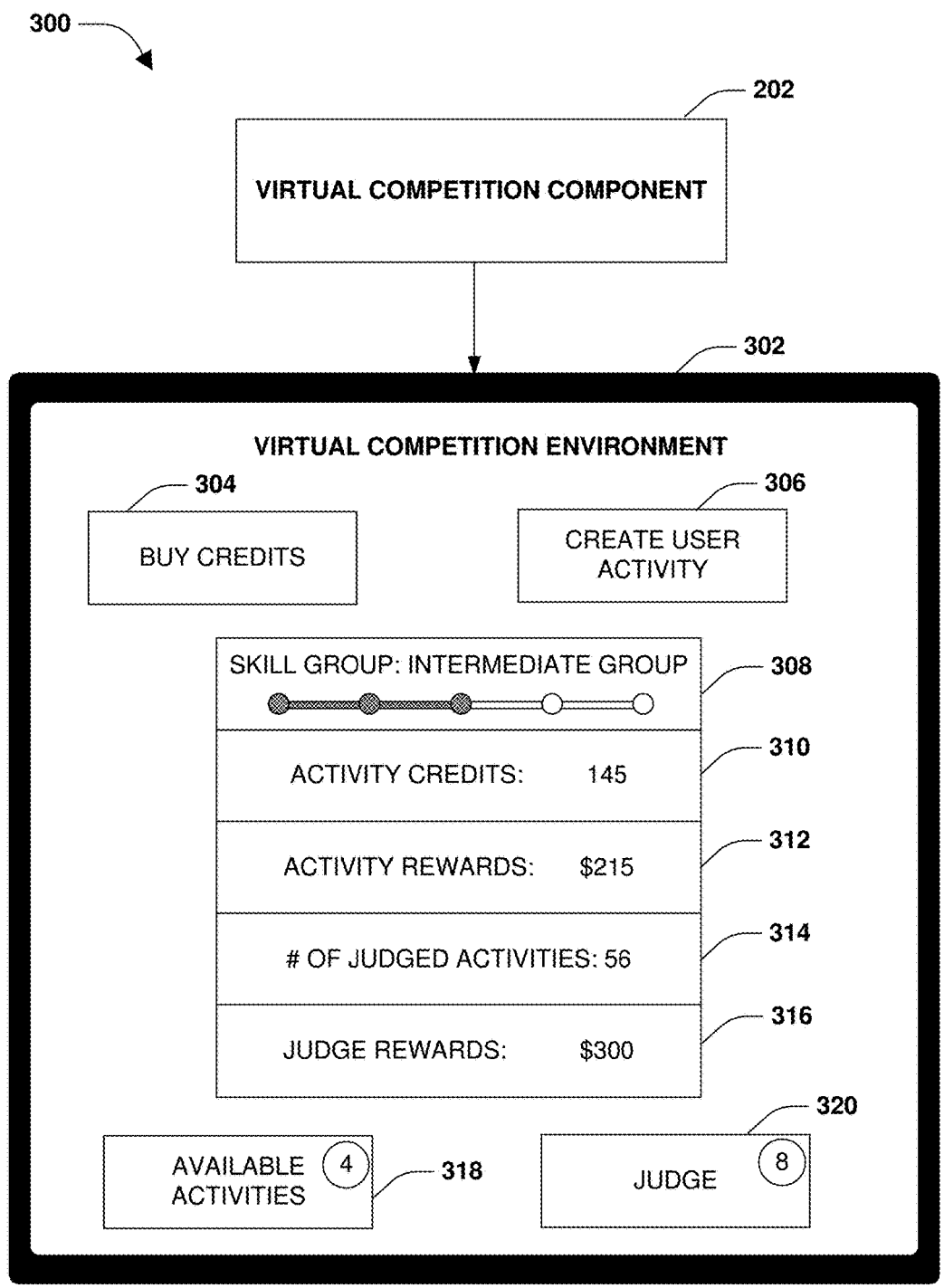
FIG. 3 is a component block diagram illustrating an exemplary system for facilitating a virtual competition environment.

FIG. 3 illustrates an example of a system 300 for facilitating a virtual competition environment 302. The system 300 comprises a virtual competition component 202. The virtual competition component 202 may be configured to provide one or more registered users, such as a first user, with access to the virtual competition environment 302. The virtual competition environment 302 may comprise a credit purchasing interface 304 through which the first user may purchase activity credits used to participate in activity assignments. For example, the first user may view, purchase, and/or request activities through an available activities interface 318 (e.g., the available activities interface 318 may provide an alert that 4 activities are accessible for the first user). The virtual competition environment 302 may comprise a skill group indicator 308. The skill group indicator 308 may indicate a skill group into which the first user is grouped, such as an intermediate skill group. The virtual competition environment 302 may comprise an activity credits interface 310 that specifies a number of activity credits that the first user has available for participating in activity assignments, creating user activities, creating and/or participating in challenge activities, etc. The virtual competition environment 302 may comprise an activity rewards interface 312 that specifies an amount of money that the first user has earned from participating in activities, such as achieving a relatively high rank for activity assignments, challenge activities, user created activities, etc.

In an example, the first user may be registered with the virtual competition environment 302 as a judge (e.g., the first user may submit various credentials corresponding to one or more types of activities for which the first user is certified or knowledgeable). The first user may access various activity evaluation information using a judge interface 320 (e.g., the judge interface 320 may provide an alert that 8 activity results may be available for the first user to view and/or evaluate as a judge). The virtual competition environment 302 may comprise a judged activities interface 314 that may specify a number of activities that the first user has judged. The virtual competition environment 302 may comprise a judge awards interface 316 specifying an amount of monetary compensation that the first user has earned for evaluating activities.

Figure 4A:
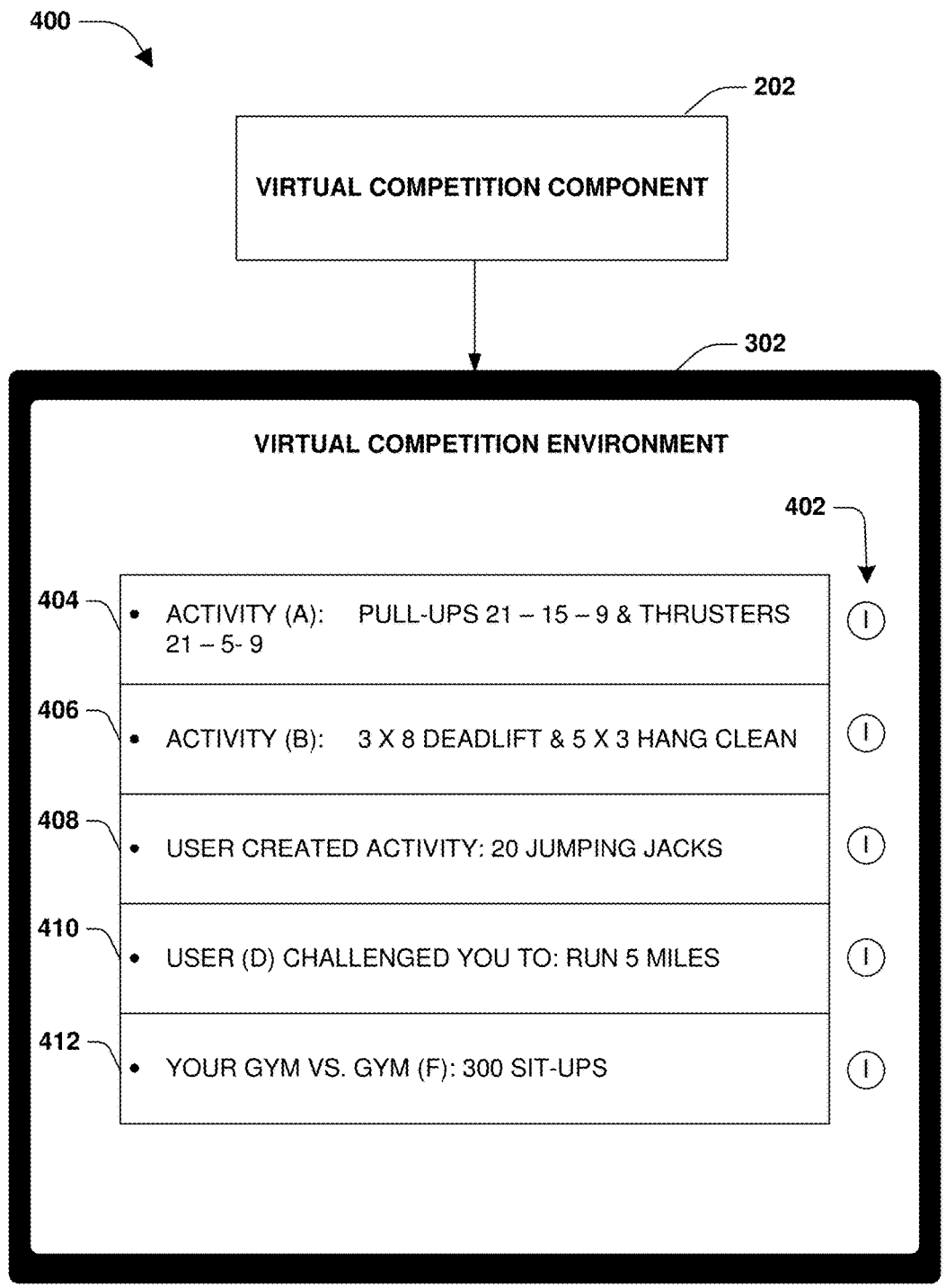
FIG. 4A is a component block diagram illustrating an exemplary system for facilitating a virtual competition environment for workout activities.

FIG. 4A illustrates an example of a system 400 for facilitating a virtual competition environment 302. The system 400 may comprise a virtual competition component 202 that may be configured to provide one or more registered users, such as a first user, with access to the virtual competition environment 302. In an example, the first user may specify an interest in workout activities. Accordingly, the virtual competition component 202 may provide various workout activity assignments to the first user. In an example, an activity assignment (A) 404 may correspond to pull-ups and thrusters. In another example, an activity assignment (B) 406 may correspond to deadlifts and hang cleans. In another example, a user created activity 408 may correspond to jumping jacks (e.g., a second user, registered with the virtual competition environment 302, may create the user created activity 408 so that other users may participate in the user created activity 408). In another example, a user challenge activity 410 may correspond to a 5 mile run (e.g., the second user may challenge the first user to a 5 mile run, where the users may be given an opportunity to place credit bets or not on who will win). In another example, a challenge activity 412 may correspond to a 300 sit-up challenge between a first gym with which the first user is a member and a gym (F). In an example, at least one of the activity assignment (A) 404, the activity assignment (B) 406, the user created activity 408, the user challenge activity 410, and/or the challenge activity 412 may be provided to the first user for free. In another example, at least one of the activity assignment (A) 404, the activity assignment (B) 406, the user created activity 408, the user challenge activity 410, and/or the challenge activity 412 may be purchased by the first user using activity credits.

Figure 4B:
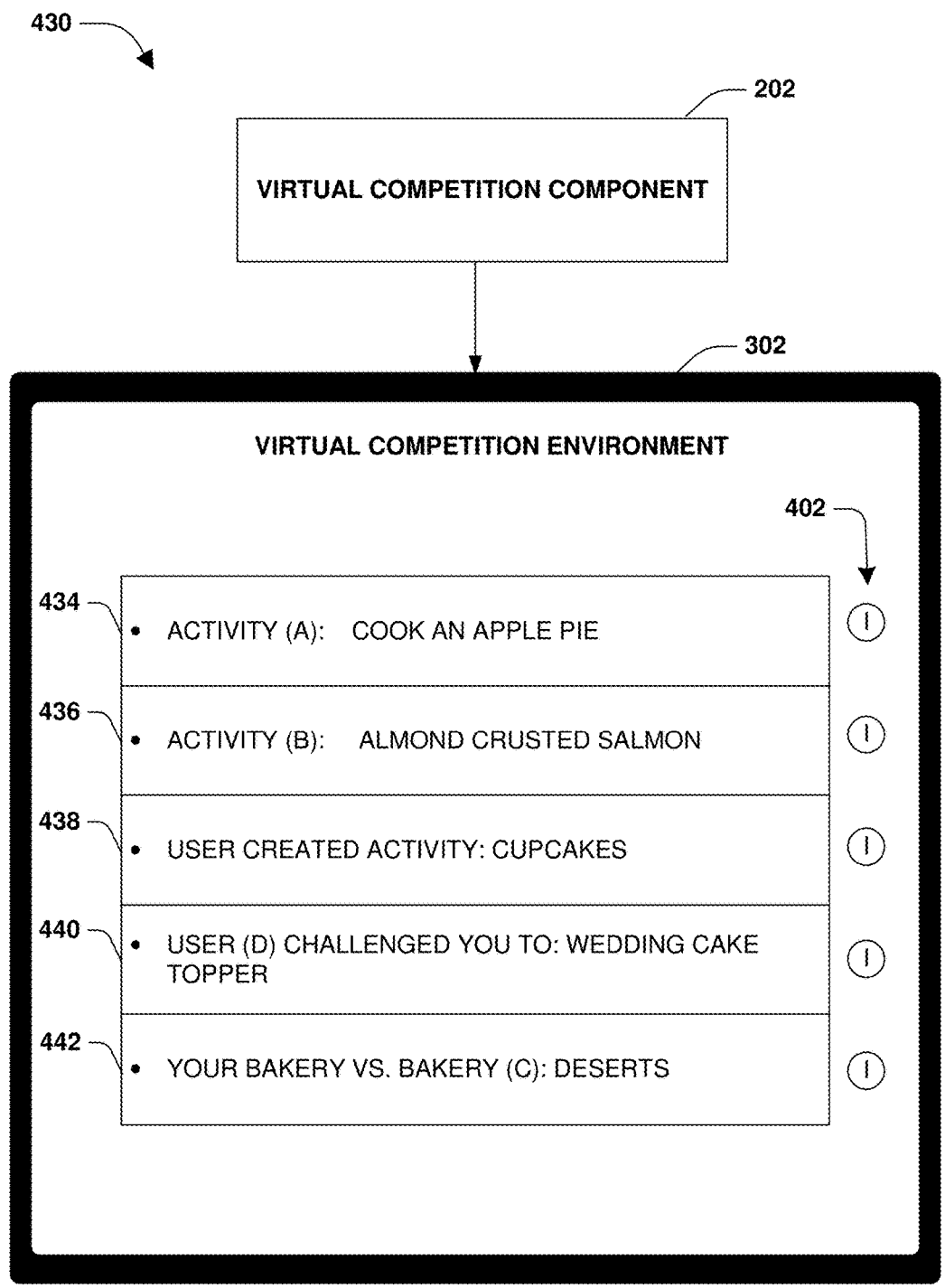
FIG. 4B is a component block diagram illustrating an exemplary system for facilitating a virtual competition environment for cooking activities.
Figure 4C:
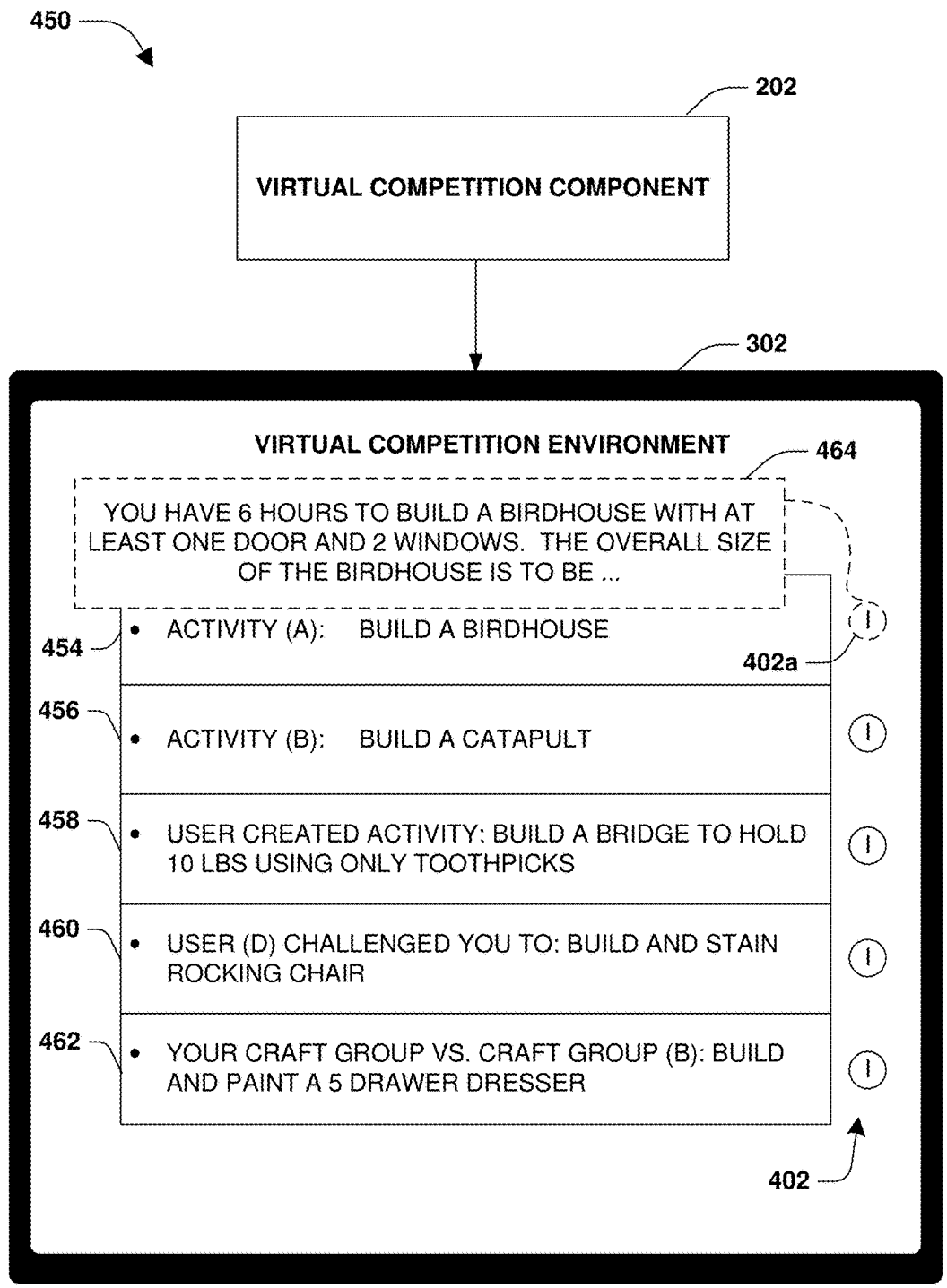
FIG. 4C is a component block diagram illustrating an exemplary system for facilitating a virtual competition environment for item construction and/or crafting activities.

The virtual competition environment 402 may provide information interfaces 402 that may be invoked by the first user to view additional details relating to an activity (e.g., FIG. 4C). For example, a video clip of the activity being performed, textual instructions, images, a question/answer interface, additional constraints for the activity, user ratings/reviews for an activity, and/or a variety of other information may be provided for the activity.

FIG. 4B illustrates an example of a system 430 for facilitating a virtual competition environment 302. The system 430 may comprise a virtual competition component 202 that may be configured to provide one or more registered users, such as a first user, with access to the virtual competition environment 302. In an example, the first user may specify an interest in cooking activities. Accordingly, the virtual competition component 202 may provide various cooking activity assignments to the first user. In an example, an activity assignment (A) 434 may correspond to cooking an apple pie. In another example, an activity assignment (B) 436 may correspond to creating an almond crusted salmon. In another example, a user created activity 438 may correspond to decorating cupcakes (e.g., a second user, registered with the virtual competition environment 302, may create the user created activity 438 so that other users may participate in the user created activity 438). In another example, a user challenge activity 440 may correspond to creating a wedding cake topper (e.g., the second user may challenge the first user to create a Halloween wedding cake topper). In another example, a challenge activity 442 may correspond to a desert challenge between a first bakery with which the first user is a member and a bakery (C). In an example, at least one of the activity assignment (A) 434, the activity assignment (B) 436, the user created activity 438, the user challenge activity 440, and/or the challenge activity 442 may be provided to the first user for free. In another example, at least one of the activity assignment (A) 434, the activity assignment (B) 436, the user created activity 438, the user challenge activity 440, and/or the challenge activity 442 may be purchased by the first user using activity credits.

FIG. 4C illustrates an example of a system 450 for facilitating a virtual competition environment 302. The system 450 may comprise a virtual competition component 202 that may be configured to provide one or more registered users, such as a first user, with access to the virtual competition environment 302. In an example, the first user may specify an interest in item construction and/or crafting activities. Accordingly, the virtual competition component 202 may provide various item construction and/or crafting activity assignments to the first user. In an example, an activity assignment (A) 454 may correspond to building a birdhouse. Responsive to the first user invoking an information interface 402a for the activity assignment (A) 454, a textual description 464 comprising instructions for the activity assignment (A) 454 may be displayed. In another example, an activity assignment (B) 456 may correspond to building a catapult. In another example, a user created activity 458 may correspond to building a bridge from toothpicks, such that the bridge can hold 10 lbs. (e.g., a second user such as a school teach of the first user, registered with the virtual competition environment 302, may create the user created activity 458 so that other users may participate in the user created activity 458). In another example, a user challenge activity 460 may correspond to building and staining a rocking chair (e.g., the second user may challenge the first user in a rocking chair building competition). In another example, a challenge activity 462 may correspond to building a 5 drawer dresser between a first craft group with which the first user is a member and a craft group (B). In an example, at least one of the activity assignment (A) 454, the activity assignment (B) 456, the user created activity 458, the user challenge activity 460, and/or the challenge activity 462 may be provided to the first user for free. In another example, at least one of the activity assignment (A) 454, the activity assignment (B) 456, the user created activity 458, the user challenge activity 460, and/or the challenge activity 462 may be purchased by the first user using activity credits.

Figure 4D:
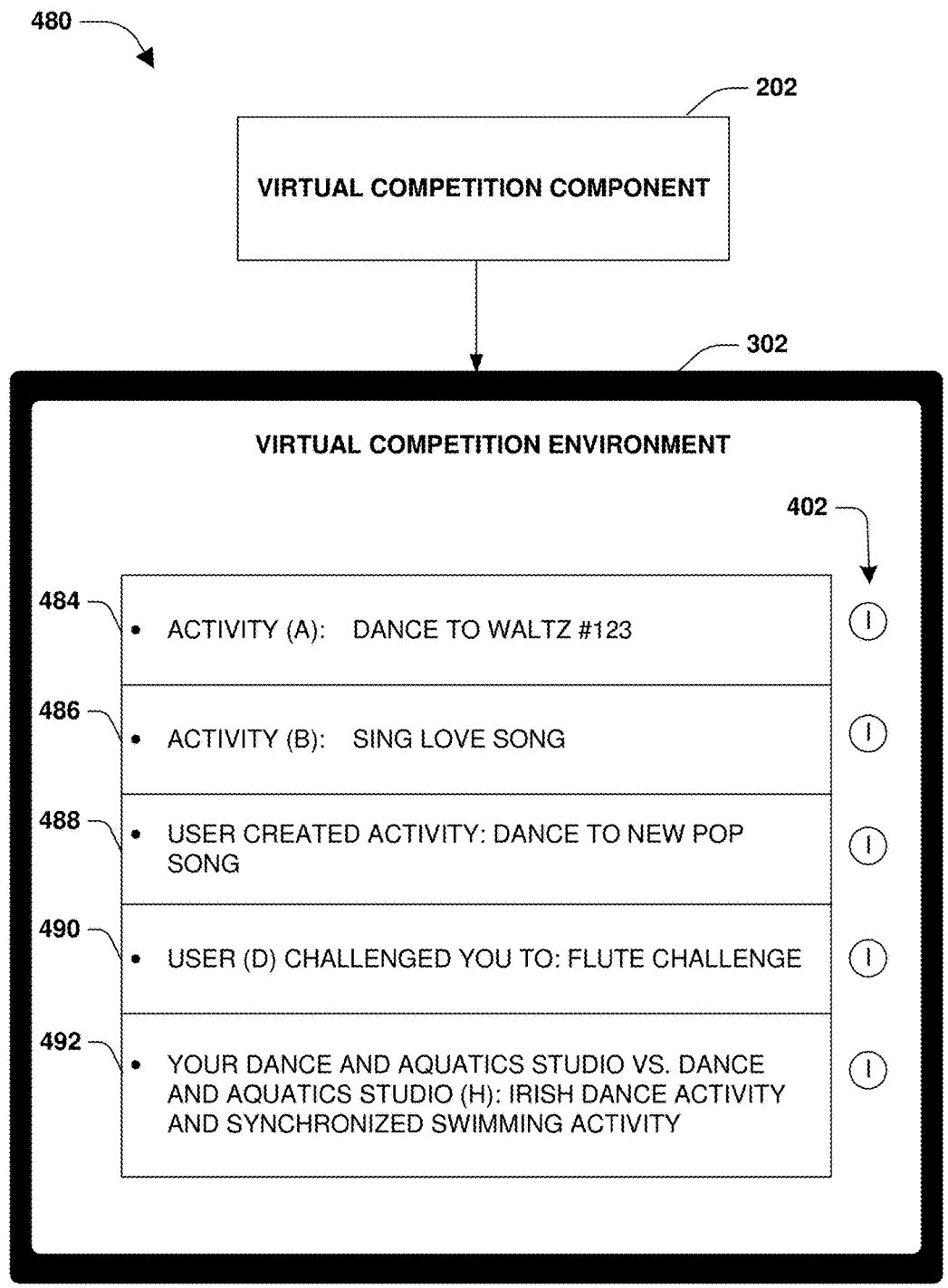
FIG. 4D is a component block diagram illustrating an exemplary system for facilitating a virtual competition environment for dance activities.

FIG. 4D illustrates an example of a system 480 for facilitating a virtual competition environment 302. The system 480 may comprise a virtual competition component 202 that may be configured to provide one or more registered users, such as a first user, with access to the virtual competition environment 302. In an example, the first user may specify an interest in dance activities. Accordingly, the virtual competition component 202 may provide various dance activity assignments to the first user. In an example, an activity assignment (A) 484 may correspond to a waltz dance. In another example, an activity assignment (B) 486 may correspond to writing and singing love songs. In another example, a user created activity 488 may correspond to dancing to a new pop song (e.g., a second user, registered with the virtual competition environment 302, may create the user created activity 488 so that other users may participate in the user created activity 488). In another example, a user challenge activity 490 may correspond to a flute challenge (e.g., the second user may challenge the first user to play a particular song with a flute). In another example, a challenge activity 492 may correspond to a combination of an Irish dance activity and a synchronized swimming activity between a first dance and aquatics studio with which the first user is a member and a dance and aquatics studio (H). In an example, at least one of the activity assignment (A) 484, the activity assignment (B) 486, the user created activity 488, the user challenge activity 490, and/or the challenge activity 492 may be provided to the first user for free. In another example, at least one of the activity assignment (A) 484, the activity assignment (B) 486, the user created activity 488, the user challenge activity 490, and/or the challenge activity 492 may be purchased by the first user using activity credits.

Figure 5A:
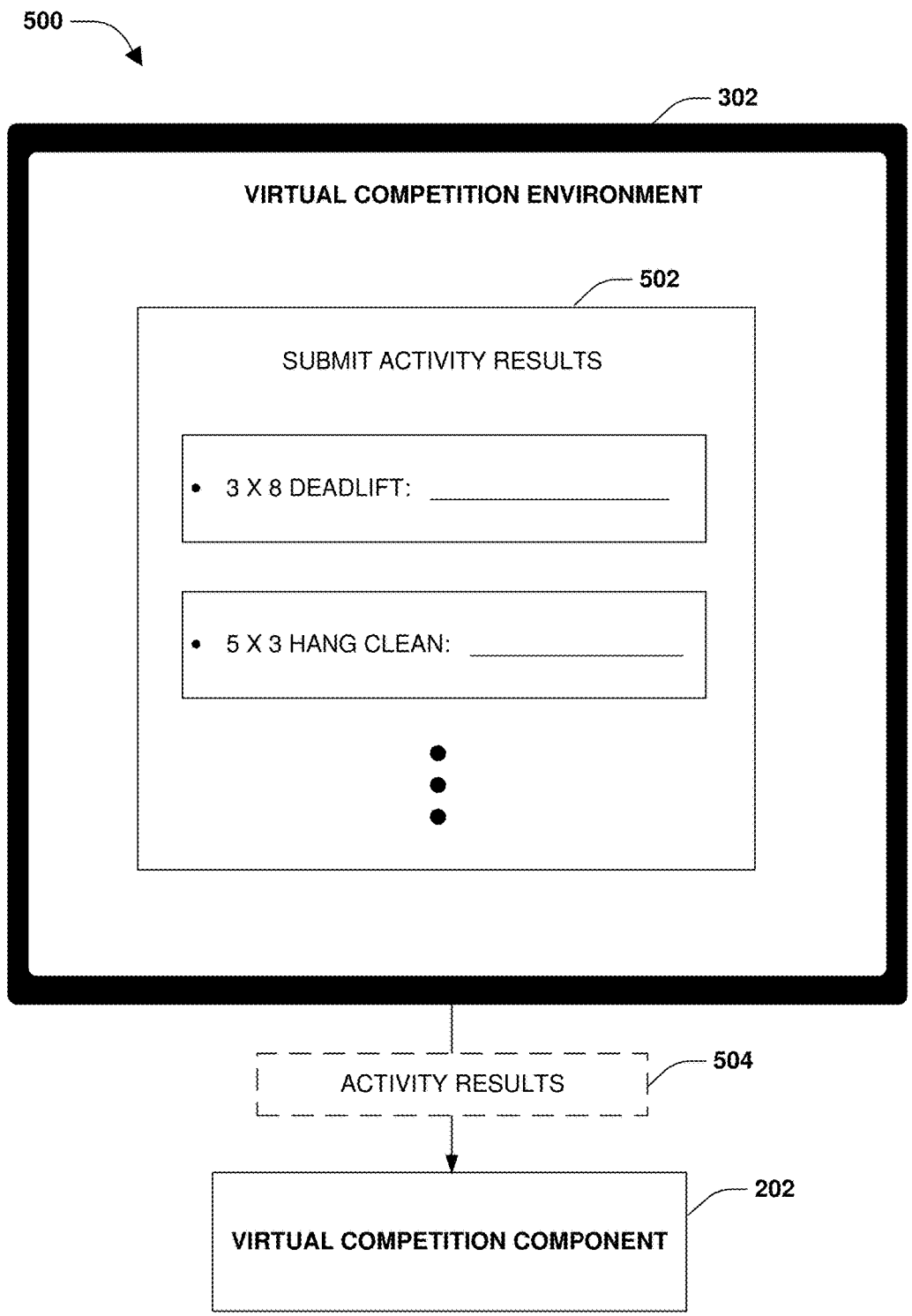
FIG. 5A is an illustration of an example of an activity submission interface of a virtual competition environment.
Figure 5B:
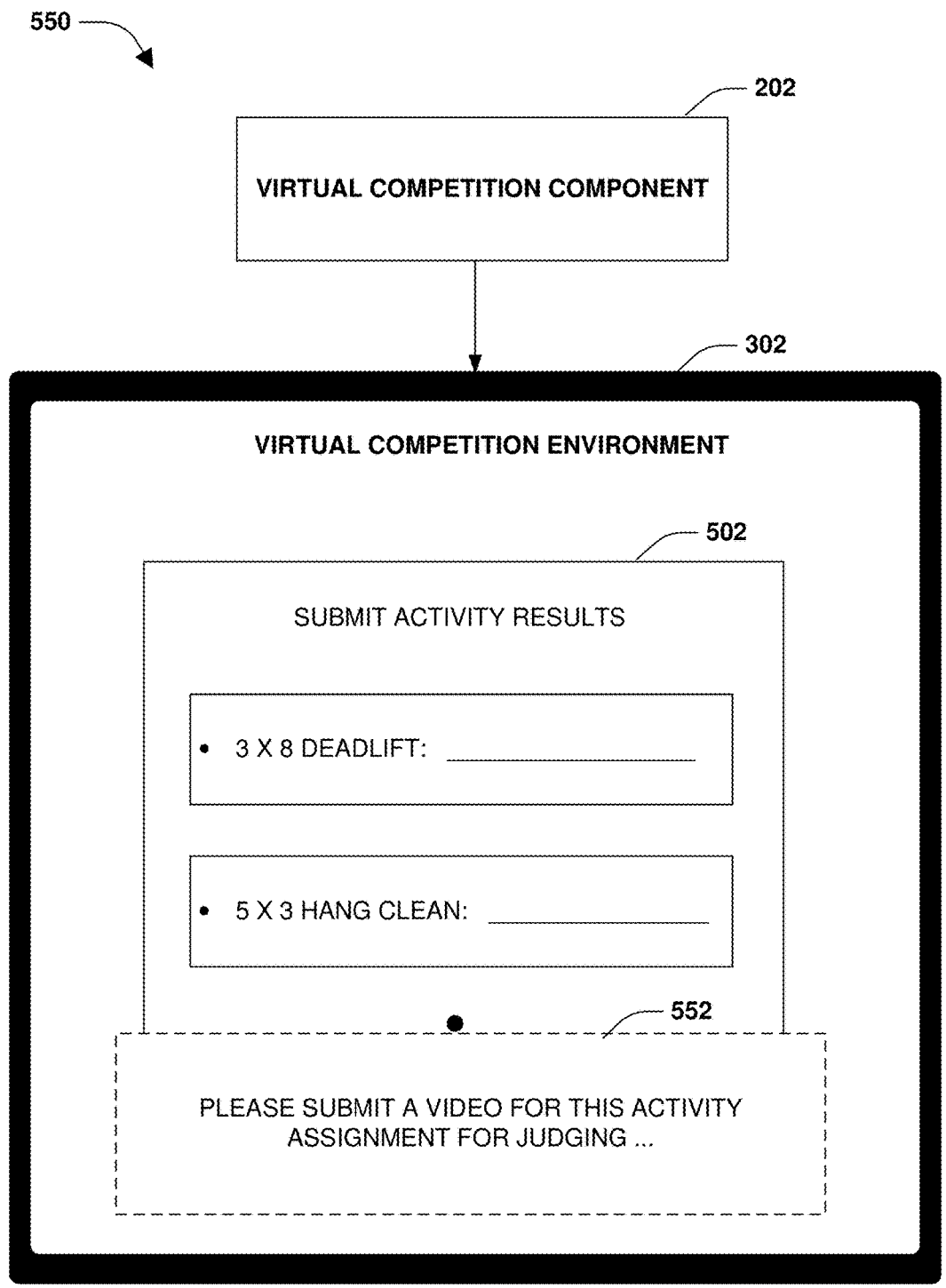
FIG. 5B is an illustration of an example of a video submission interface of an activity submission interface.

FIG. 5A illustrates an example 500 of an activity submission interface 502 of a virtual competition environment 302. A virtual competition component 202 may be configured to provide one or more registered users, such as a first user, with access to the virtual competition environment 302. The first user may be provided with activity assignments, user created activities, challenge activities, and/or other activities with which the first user may participate. For example, the first user may participate in an activity assignment (B) 406 corresponding to deadlifts and hang cleans (e.g., FIG. 4A). The virtual competition environment 302 may provide the activity submission interface 502 first user so that the first user may submit activity results 504 for the activity assignment (B) 406 (e.g., textual results, an image, a video, etc.). The virtual competition component 202 may receive the activity results 504, which may be evaluated to assign an activity rank to the first user with regard to the activity assignment (B) 406. In an example, the first user may have a participant rank (e.g., based upon the activity results 504 for the activity assignment (B) 406 and/or based upon historical activity results for the first user) above a threshold (e.g., a top 5% of participants for the activity assignment (B) 406). Accordingly, a video submission interface 552 may be provided to the first user so that the first user may submit a video for evaluation by a judge as to how the first user performed the activity assignment (B) 406, as illustrated in example 550 of FIG. 5B.

Figure 6:
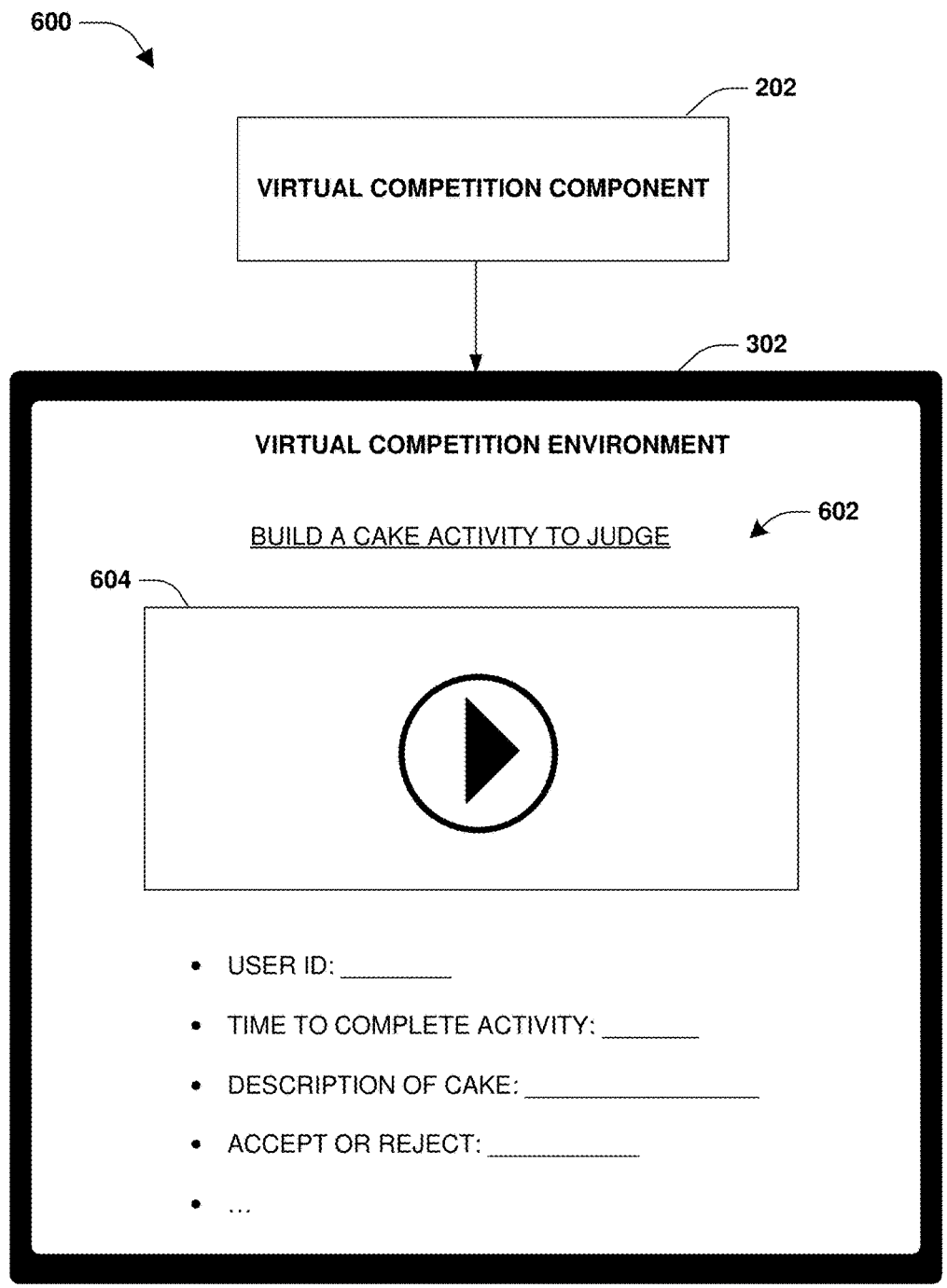
FIG. 6 is an illustration of an example of a judge review interface of a virtual competition environment.

FIG. 6 illustrates an example 600 of a judge review interface 602 of a virtual competition environment 302. Users of the virtual competition environment 302 may register as judges in order to evaluate activity results of users performing various types of activities. A virtual competition component 202 may provide the judge review interface 602 to a first judge registered for judging cooking activities. The judge review interface 602 may provide a video 604 of a user performing a cake building activity. The first judge may specify various information about judging the cake building activity through the judge review interface 602, such as a user ID spoken by the user, a time that it took for the user to finish the cake building activity, a description of the cake, whether the judge accepts or rejects the video, etc. In an example, if the first judge rejects the video, then the user may appeal the rejection. For example, the user may be provided with an appeal time limit within which the user may submit an appeal. If the users submits the appeal within the appeal time limit, then the video is provided to a second judge for evaluation. If the second judge rejects the video, then the rejection of the video is finalized. If the second judge accepts the video, then the video is provided to a third judge for evaluation. The decision of the third judge to accept or reject the video may be a finalized decision (e.g., a majority rule between the third judges). In an example, the first judge may be constrained to a time limit with which the first judge is to review the video before the video is provided to a second judge for evaluation. In this way, the user may be assigned an activity rank for the cake building activity by the first judge.

Figure 7:
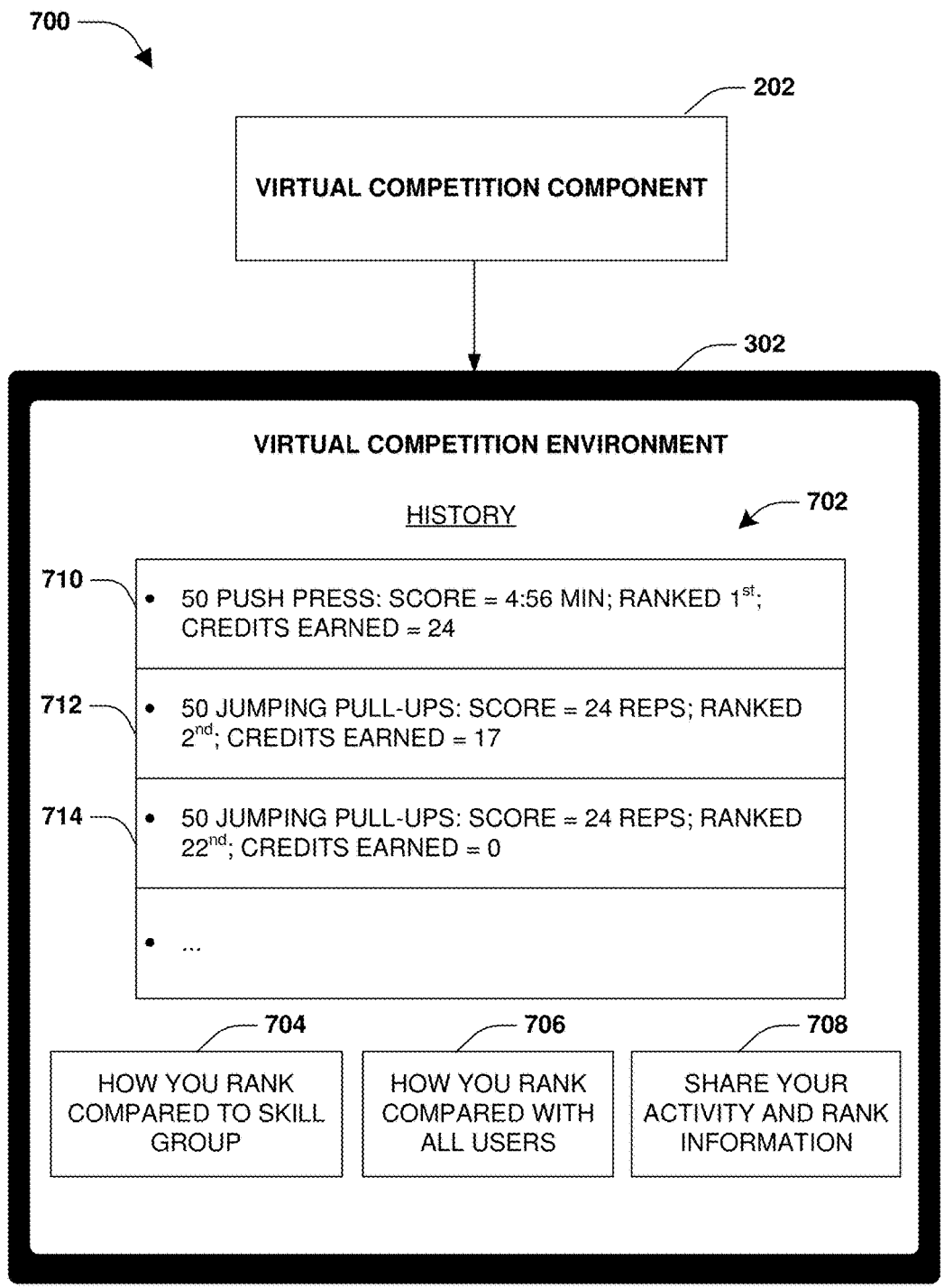
FIG. 7 is an illustration of an example of a performance interface of a virtual competition environment.

FIG. 7 illustrates an example of a performance interface 702 of a virtual competition environment 302. A virtual competition component 202 may be configured to provide one or more registered users, such as a first user, with access to a virtual competition environment 302. The first user may perform various activities, such as activity assignments, user created activities, and/or challenge activities, which may be ranked against other users that performed such activities. The performance interface 702 may provide historical activity results and/or activity ranks associated with the first user, such as a push press activity summary 710, a first jumping pull-ups activity summary 712, a second jumping pull-ups activity summary 714, and/or other activity summaries not illustrated. An activity summary may specify an activity rank awarded for an activity assignment (e.g., a first place activity rank), credits earned for the activity assignment (e.g., 24 credits), and activity results for the activity assignment (e.g., 4:56 min to perform 50 push presses). The performance interface 702 may provide a skill group rank interface 704 through which the first user may view how the first user ranks against other users within a skill group with which the first user is assigned. The performance interface 702 may provide a global rank interface 706 through which the first user may view how the first user ranks against other users of the virtual competition environment 302. The performance interface 702 may provide a social interface 708 through which the first user may share activity results and/or activity ranking information (e.g., send through an email; post to a social network; post to a website; post as a microblog message; etc.).

Figure 8:
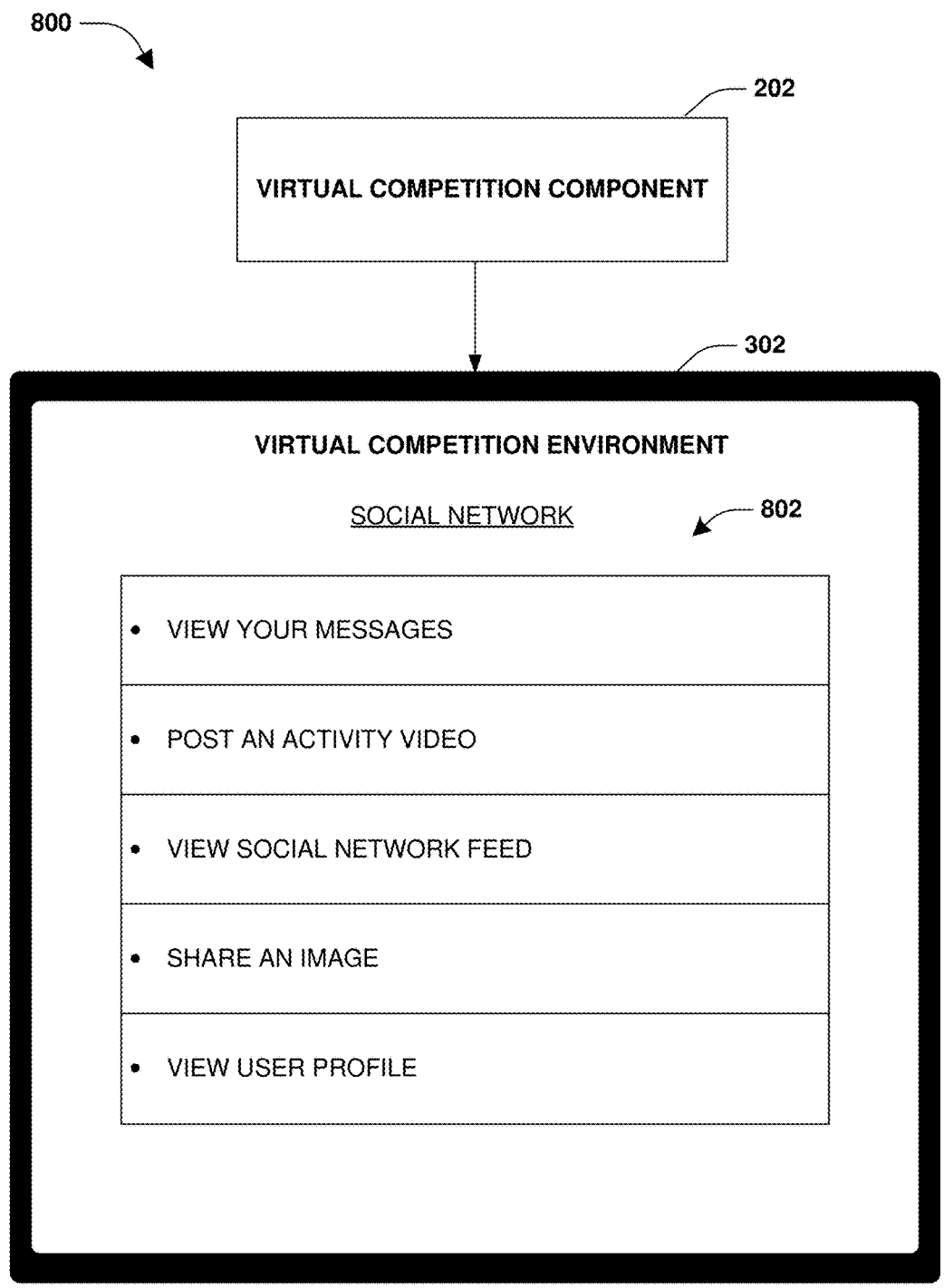
FIG. 8 is an illustration of an example of a social network interface of a virtual competition environment.

FIG. 8 illustrates an example 800 of a social network interface 802 of a virtual competition environment 302. The social network interface 802 may allow a user to view/send messages, post an activity video to a social network profile of the user, view social network feed information (e.g., activities, rankings, or other information shared by other users of the virtual competition environment 302), share an image, view user profiles, and/or perform a variety of other social network activities with other users of the virtual competition environment 302.

In some embodiments, a sensor (e.g., a GPS unit, an inertial measurement unit (MU), a radio detection and ranging (RADAR) unit, a laser rangefinder and/or light detection and ranging (LIDAR) unit, a camera, etc.) may be used to perform at least some of the acts described herein and/or to determine at least some of the measurements discussed herein. For example, a sensor (e.g., a camera, a motion tracking sensor, etc.) may be used to identify physical attributes of a user. The sensor may be coupled to a mobile device (e.g., cell phone) of the user, or exercise equipment (e.g., barbell) associated with (e.g., used by) the user. The physical attributes may comprise a dimension of a portion of a body of the user, such as a length of an arm of the user, a width of a leg of the user, a height of the user, etc.

In some embodiments, a sensor may be used to monitor movement of a user. For example, the sensor may be used to determine a number of exercise movements performed (e.g., reps, sets, etc.), distance traveled during a squat, distance traveled when a weight is placed over the user's head with arms fully extended, etc. The sensor may be stationary during movement, or may be moved (e.g., and the motion of the sensor may be used for the monitoring).

In some embodiments, a sensor (e.g., with body image tracking, coupled to a video game console, a computer, etc.) may be used to determine whether the user performed an activity result in accordance with requirements associated with the activity result. For example, the sensor may be used to determine whether the user performed a full range of motion and/or otherwise met a movement standard (e.g., as defined for the activity result). For example, the sensor may be used to determine whether the user squat below parallel, reached full extension with weight above their head, cross elbows over the proper plane when they caught the weight in a front squat position, etc. Such a determination may be performed as part of evaluation of the first activity result, and may, for example, influence the assignment of an activity rank. For example, if a determination is made that the user did perform a full range of motion in one or more activities, the user may be assigned a higher activity rank than a second user that is determined to have not performed a full range of motion in the one or more activities. It may be appreciated that the determination of whether the user performed a full range of motion may be one of a plurality of factors used to evaluate the first activity result and/or to assign activity rank.

In some embodiments, an output wattage may be determined for a user based upon a combination of a number of exercise movements that the user has been determined (e.g., by a sensor) to have performed, a weight of the user, and/or physical attributes comprising a dimension (e.g., length) of a portion of the body (e.g., leg, arm, etc.) of the user. For example, the weight of the user (e.g., which may be manually input by the user, or determined by a sensor, etc.) may be combined with (e.g., multiplied by) the dimension of the portion of the body and further combined with (e.g., multiplied by) the number of exercise movements that the user has been determined to have performed to determine the output wattage.

Figure 9:
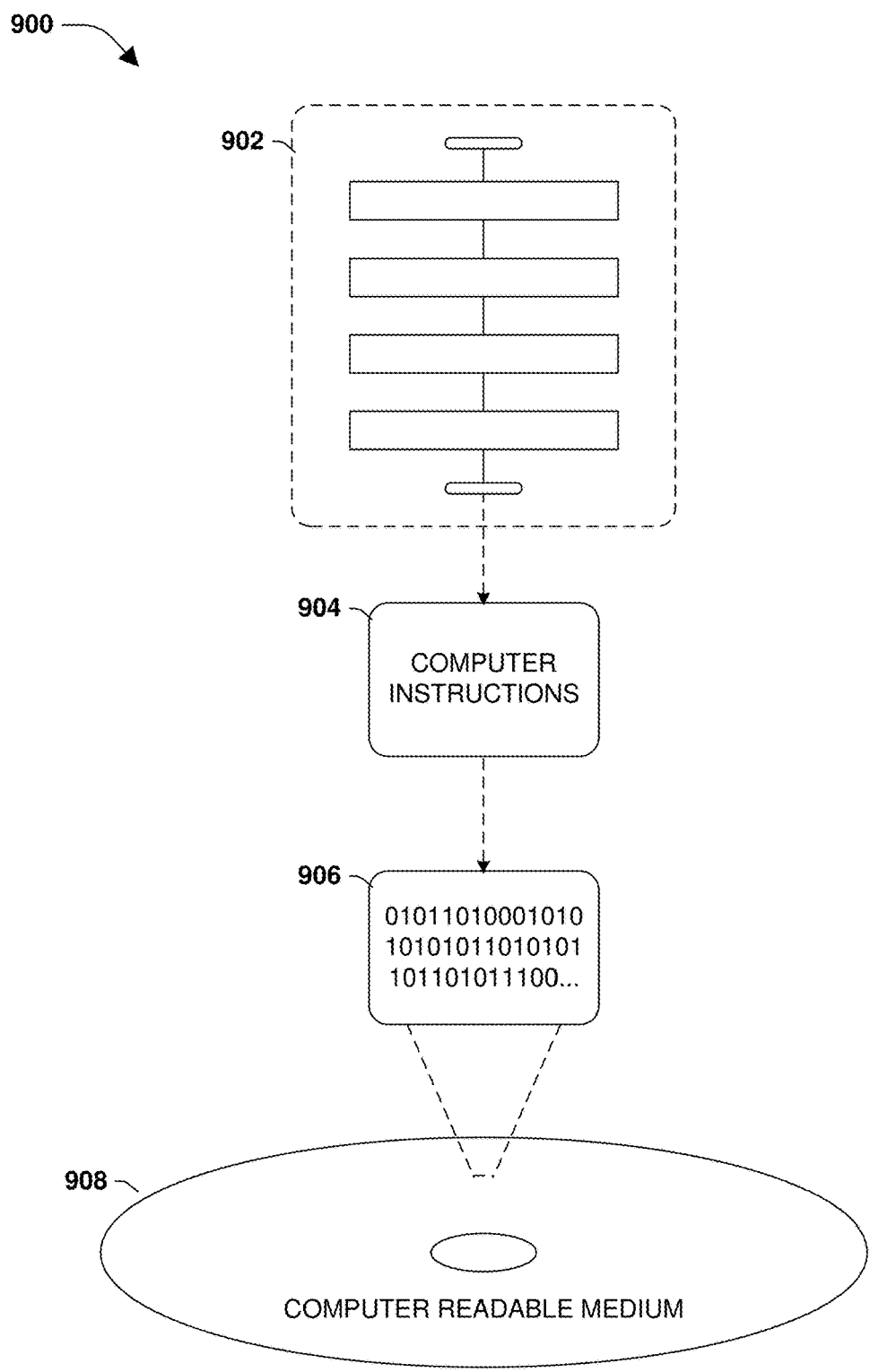
FIG. 9 is an illustration of an exemplary computer readable medium wherein processor-executable instructions configured to embody one or more of the provisions set forth herein may be comprised.

Still another embodiment involves a computer-readable medium comprising processor-executable instructions configured to implement one or more of the techniques presented herein. An example embodiment of a computer-readable medium or a computer-readable device is illustrated in FIG. 9, wherein the implementation 900 comprises a computer-readable medium 908, such as a CD-ft DVD-R, flash drive, a platter of a hard disk drive, etc., on which is encoded computer-readable data 906. This computer-readable data 906, such as binary data comprising at least one of a zero or a one, in turn comprises a set of computer instructions 904 configured to operate according to one or more of the principles set forth herein. In some embodiments, the processor-executable computer instructions 904 are configured to perform a method 902, such as at least some of the exemplary method 100 of FIG. 1, for example. In some embodiments, the processor-executable instructions 904 are configured to implement a system, such as at least some of the exemplary system 200 of FIG. 2, at least some of the exemplary system 300 of FIG. 3, at least some of the exemplary system 400 of FIG. 4A, at least some of the exemplary system 430 of FIG. 4B, at least some of the exemplary system 450 of FIG. 4C, at least some of the exemplary system 480 of FIG. 4D, at least some of the exemplary system 500 of FIG. 5, and/or at least some of the exemplary system 600 of FIG. 6, for example. Many such computer-readable media are devised by those of ordinary skill in the art that are configured to operate in accordance with the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

As used in this application, the terms "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 10:
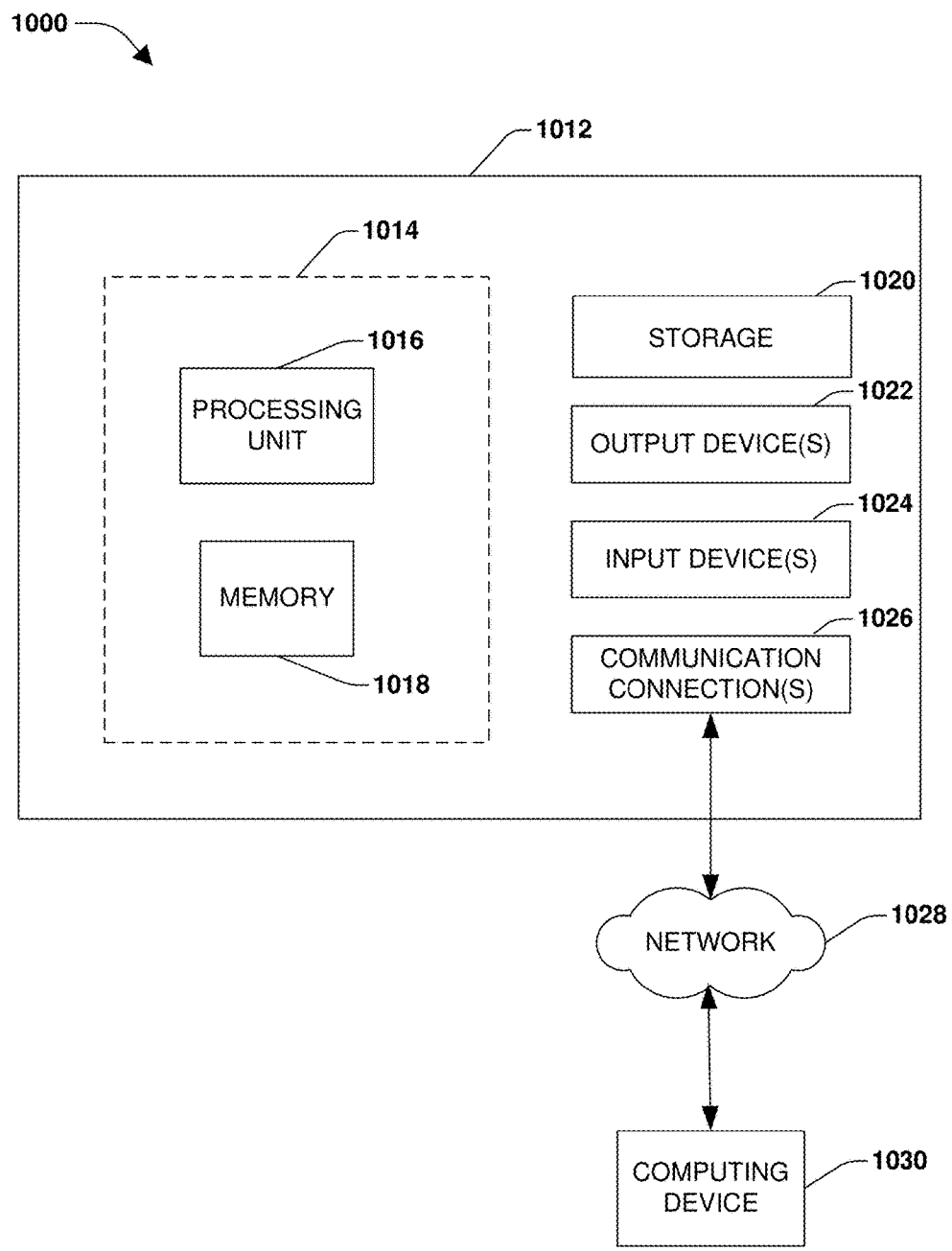
FIG. 10 illustrates an exemplary computing environment wherein one or more of the provisions set forth herein may be implemented.

FIG. 10 and the following discussion provide a brief, general description of a suitable computing environment to implement embodiments of one or more of the provisions set forth herein. The operating environment of FIG. 10 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 10 illustrates an example of a system 1000 comprising a computing device 1012 configured to implement one or more embodiments provided herein. In one configuration, computing device 1012 includes at least one processing unit 1016 and memory 1018. Depending on the exact configuration and type of computing device, memory 1018 may be volatile (such as RAM, for example), non-volatile (such as ROM, flash memory, etc., for example) or some combination of the two. This configuration is illustrated in FIG. 10 by dashed line 1014.

In other embodiments, device 1012 may include additional features and/or functionality. For example, device 1012 may also include additional storage (e.g., removable and/or non-removable) including, but not limited to, magnetic storage, optical storage, and the like. Such additional storage is illustrated in FIG. 10 by storage 1020. In one embodiment, computer readable instructions to implement one or more embodiments provided herein may be in storage 1020. Storage 1020 may also store other computer readable instructions to implement an operating system, an application program, and the like. Computer readable instructions may be loaded in memory 1018 for execution by processing unit 1016, for example.

The term "computer readable media" as used herein includes computer storage media. Computer storage media includes volatile and nonvolatile, removable and non-removable media implemented in any method or technology for storage of information such as computer readable instructions or other data. Memory 1018 and storage 1020 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 1012. Any such computer storage media may be part of device 1012.

Device 1012 may also include communication connection(s) 1026 that allows device 1012 to communicate with other devices. Communication connection(s) 1026 may include, but is not limited to, a modem, a Network Interface Card (NIC), an integrated network interface, a radio frequency transmitter/receiver, an infrared port, a USB connection, or other interfaces for connecting computing device 1012 to other computing devices. Communication connection(s) 1026 may include a wired connection or a wireless connection. Communication connection(s) 1026 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 1012 may include input device(s) 1024 such as keyboard, mouse, pen, voice input device, touch input device, infrared cameras, video input devices, and/or any other input device. Output device(s) 1022 such as one or more displays, speakers, printers, and/or any other output device may also be included in device 1012. Input device(s) 1024 and output device(s) 1022 may be connected to device 1012 via a wired connection, wireless connection, or any combination thereof. In one embodiment, an input device or an output device from another computing device may be used as input device(s) 1024 or output device(s) 1022 for computing device 1012.

Components of computing device 1012 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 1012 may be interconnected by a network. For example, memory 1018 may be comprised of multiple physical memory units located in different physical locations interconnected by a network.

Those skilled in the art will realize that storage devices utilized to store computer readable instructions may be distributed across a network. For example, a computing device 1030 accessible via a network 1028 may store computer readable instructions to implement one or more embodiments provided herein. Computing device 1012 may access computing device 1030 and download a part or all of the computer readable instructions for execution. Alternatively, computing device 1012 may download pieces of the computer readable instructions, as needed, or some instructions may be executed at computing device 1012 and some at computing device 1030.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used herein, "or" is intended to mean an inclusive "or" rather than an exclusive "or". In addition, "a"

and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", and/or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method executed by a processor, the method comprising:
registering a first user for access to a virtual competition environment accessible through a user interface displayed on a display of a computing device;
using a hardware sensor coupled to the computing device of the first user or exercise equipment of the first user to identify physical attributes comprising a dimension of a portion of a body of the first user, wherein the computing device receives sensor data from the hardware sensor over a communication link;
performing, by the processor, a power output calculation for the first user based upon a combination of a determined number of exercise movements, a weight of the first user and the physical attributes comprising the dimension of the portion of the body of the first user to determine an output wattage for the first user;
utilizing the output wattage to assign the first user to a first skill group;
generating and displaying a first activity assignment for the first skill group through the user interface displayed on the computing device;
responsive to receiving, by the computing device, a first activity result of the first user for the first activity assignment, evaluating the first activity result using a second hardware sensor to determine whether the first user performed the first activity result in accordance with requirements for a full range of motion, wherein the computing device receives second sensor data from the second hardware sensor over a second communication link;
responsive to determining that the first user has a participant rank above a threshold, triggering generation of a video of the first user performing the first activity assignment;
transmitting the video to second computing device of a judge registered with the virtual competition environment for evaluation of the video; and
generating a first activity rank based upon evaluation of the video by the judge.

2. The method of claim 1, comprising:
assigning the first user to the first skill group based upon a user profile associated with the first user; and
providing the first activity assignment to one or more users assigned to the first skill group.

3. The method of claim 1, the performing the power output calculation comprising:
utilizing at least one of a shoulder width, an arm length, a height, or a workout result of the first user to determine the output wattage.

4. The method of claim 2, the evaluating the first activity result comprising:
comparing the first activity result to a set of activity results received from the one or more users assigned to the first skill group to generate the first activity rank.

5. The method of claim 1, comprising:
sharing at least one of the first activity result or the first activity rank through at least one of a social network, a website, a leaderboard, a microblog message, an email, or an instance of the virtual competition environment on a device of a second user registered with the virtual competition environment.

6. The method of claim 1, comprising:
receiving a user created activity from the first user; and
providing the user created activity to one or more users registered with the virtual competition environment.

7. The method of claim 1, comprising:
providing the first user with a reward based upon the first activity rank, the reward corresponding to at least one of a credit used to participate in an activity, a monetary reward, or a donation to a charity.

8. The method of claim 1, comprising:
assigning the first user to a first user group based upon the first user having membership to the first user group;
generating a challenge activity between the first user group and a second user group; and
ranking activity results from the first user group with activity results from the second user group to assign rankings to at least one of the first user group, the second user group, one or more users that are members with the first user group, or one or more users that are members with the second user group.

9. The method of claim 1, comprising:
providing an evaluation time limit within which the judge is to accept the video for ranking.

10. The method of claim 1, comprising:
providing an evaluation time limit within which the judge is to reject the video for ranking.

11. The method of claim 1, comprising:
providing an evaluation time limit within which the judge is to assign an activity rank for the video.

12. The method of claim 1, comprising:
instructing the judge to verify that the first user is utilizing a valid video for the first activity assignment; and
receiving a verification from the judge.

13. The method of claim 1, comprising:
providing the judge with compensation based upon judging the video, the compensation corresponding to at least one of a credit used to participate in an activity, a monetary reward, or a donation to a charity.

14. The method of claim 1, comprising:
responsive to receiving a rejection of the video from the judge, facilitating an appeal process for the first user.

15. The method of claim 2, the providing the first activity assignment to one or more users assigned to the first skill group comprising:
responsive to the first activity assignment being assigned to a threshold number of user within the first skill group;
generating a new iteration of the first activity assignment to create a new first activity assignment; and
providing the new first activity assignment to one or more users within the first skill group.

16. The method of claim 1, the first activity assignment corresponding to a physical workout assignment to be physically performed by the first user.

17. The method of claim 1, comprising:
generating a first user profile for the first user based upon at least one of historical activity results or activity ranks associated with the first user.

18. The method of claim 1, comprising at least one of:
providing a judge review interface through which the judge evaluates activity results of users;
providing a credit purchasing interface through which the first user purchases credits for participating in activity assignments;
providing a performance interface to the first user, the performance interface displaying at least one of historical activity results or activity ranks associated with the first user; or
providing a social network interface comprising at least one of friends list functionality, messaging functionality, activity information, activity results information, activity sharing functionality, challenge invitation functionality, or social profile functionality.

19. A system for facilitating a virtual competition environment, comprising:
one or more processors; and
memory comprising instructions that when executed by at least one of the one or more processors, implement operations comprising:
registering a first user for access to a virtual competition environment accessible through a user interface displayed on a display of a computing device;
using a hardware sensor coupled to the computing device of the first user or exercise equipment of the first user to identify physical attributes comprising a dimension of a portion of a body of the first user, wherein the computing device receives sensor data from the hardware sensor over a communication link;
performing, by the processor, a power output calculation for the first user based upon a combination of a determined number of exercise movements, a weight of the first user and the physical attributes comprising the dimension of the portion of the body of the first user to determine an output wattage for the first user;
utilizing the output wattage to assign the first user to a first skill group;
generating and displaying a first activity assignment for the first skill group through the user interface displayed on the computing device;
receiving, by the computing device, a first activity result of the first user for the first activity assignment;
responsive to determining that the first user has a participant rank above a threshold, triggering generation of a video of the first user performing the first activity assignment;
transmitting the video to second computing device of a judge registered with the virtual competition environment for evaluation of the video; and
generating a first activity rank based upon evaluation of the video by the judge.

20. A computer readable medium comprising instructions which when executed at least in part via a processor perform a method comprising:
registering a first user for access to a virtual competition environment accessible through a user interface displayed on a display of a computing device;
using a hardware sensor to identify physical attributes comprising a dimension of a portion of a body of the first user;
performing, by the processor, a power output calculation for the first user based upon a combination of two or more of a determined number of exercise movements, a weight of the first user or the physical attributes comprising the dimension of the portion of the body of the first user to determine an output wattage for the first user;
utilizing the output wattage to assign the first user to a first skill group;
providing the first user with a first activity assignment for the first skill group; and
receiving a first activity result from the first user for the first activity assignment;
responsive to determining that the first user has a participant rank above a threshold, triggering generation of a video of the first user performing the first activity assignment;
transmitting the video to second computing device of a judge registered with the virtual competition environment for evaluation of the video; and
generating a first activity rank based upon evaluation of the video by the judge.

* * * * *